United States Patent
Peckham et al.

(10) Patent No.: US 10,780,075 B1
(45) Date of Patent: Sep. 22, 2020

(54) WATER SOLUBLE CANNABIS COMPOSITION

(71) Applicant: Etain IP, LLC, Katonah, NY (US)

(72) Inventors: Hillary Peckham, Katonah, NY (US); Mykola Ianchenko, Katonah, NY (US); Joseph Stevens, Vernon, NJ (US); Keeley Peckham, Katonah, NY (US)

(73) Assignee: Etain IP, LLC, Katonah, NY (US)

( * ) Notice: Subject to any disclaimer, the term of this patent is extended or adjusted under 35 U.S.C. 154(b) by 0 days.

(21) Appl. No.: 16/528,102

(22) Filed: Jul. 31, 2019

(51) Int. Cl.
| | |
|---|---|
| *A61K 36/00* | (2006.01) |
| *A61K 31/352* | (2006.01) |
| *A61K 47/46* | (2006.01) |
| *A61K 9/14* | (2006.01) |
| *A61K 47/40* | (2006.01) |
| *A61K 9/08* | (2006.01) |
| *A61K 47/38* | (2006.01) |

(52) U.S. Cl.
CPC .............. *A61K 31/352* (2013.01); *A61K 9/08* (2013.01); *A61K 9/14* (2013.01); *A61K 47/38* (2013.01); *A61K 47/40* (2013.01); *A61K 47/46* (2013.01)

(58) Field of Classification Search
CPC ...................................... A61K 36/00
See application file for complete search history.

(56) References Cited

U.S. PATENT DOCUMENTS 9,480,647 B2 * 11/2016 Benson ................. A61J 1/1443

* cited by examiner

*Primary Examiner* — Michael V Meller
(74) *Attorney, Agent, or Firm* — Stefan J. Kirchanski; Matthew J. Spark; Zuber Lawler & Del Duca LLP

(57) ABSTRACT

The invention provides a water-soluble composition comprising cannabis extract. The invention also provides methods of producing a water-soluble composition comprising cannabis extract. The invention further provides a solution comprising cannabis extract. Furthermore, the invention provides a frozen composition, a medication, a pharmaceutical composition, and a kit comprising a water-soluble composition comprising cannabis extract.

26 Claims, 1 Drawing Sheet

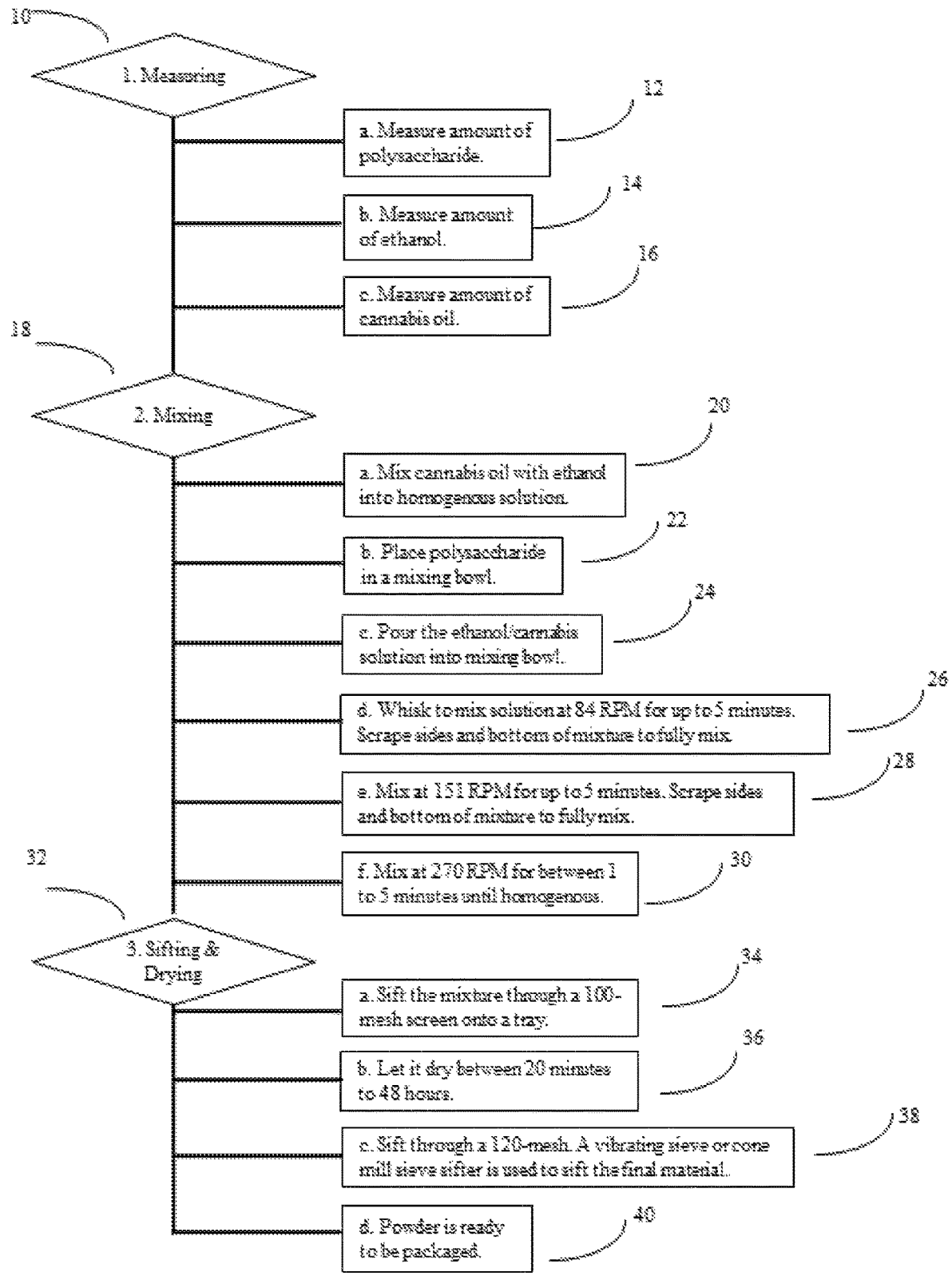

WATER SOLUBLE CANNABIS COMPOSITION

BACKGROUND OF THE INVENTION

Area of the Art

Embodiments of the present invention relate to a water-soluble powder composition comprising cannabis oil and methods to produce the water-soluble powder composition. The cannabis plant has many naturally occurring substances that are of interest in medicine, food, beverages, and cosmetics. Extracted compounds from the cannabis plant include THC (tetrahydrocannabinol), THCA (tetrahydrocannabinolic acid), CBD (cannabidiol), CBDA (cannabidiolic acid), CBN (cannabinol), CBG (cannabigerol), CBC (cannabichromene), CBL (cannabicyclol), CBV (cannabivarin), THCV (tetrahydrocannabivarin), CBDV (cannabidivarin), CBCV (cannabichromevarin), CBGV (cannabigerovarin), CBGM (cannabigerol monomethyl ether), CBE (cannabielsoin), CBT (cannabicitran), among other compounds. Extracted compounds from the cannabis plant are called cannabinoids. A cannabinoid is also defined as a class of diverse chemical compounds that interact with the endocannabinoid system in cells. There are over one hundred and forty four (144) cannabinoids that have been identified in extracts from the cannabis plant. Many studies have confirmed the medicinal value of cannabinoids. Cannabinoids have been investigated for possible treatment of seizures, nausea, vomiting, lack of appetite, pain, arthritis, inflammation, and other conditions.

Cannabis extracts may contain cannabis oil comprising cannabinoids and other beneficial components such as terpenoids. Cannabis oils are not soluble in water. The invention describes a water-soluble powder formulation comprising cannabis extract that produces a clear solution when mixed in water at various temperatures. The clear solution is shelf stable through freezing and thawing cycles. The invention also describes methods to produce the water-soluble powder composition comprising cannabis extract.

Description of the Background Art

While there are soluble compositions comprising cannabinoids in the market, these compositions have complex formulae and/or use alcohol and/or use milk, which can be allergenic or are unsuitable for use by certain populations.

One soluble formulation comprising cannabinoids is a tincture. For example, Epidiolex® is an oral solution approved by the Food and Drug Administration (FDA) for treatment of seizures associated with two rare and severe forms of epilepsy, Lennox-Gastaut syndrome and Dravet syndrome. Epidiolex® oral solution consists of cannabidiol at a concentration of 100 mg/mL, and ingredients such as dehydrated alcohol, sesame seed oil, strawberry flavor, and sucralose. However, alcohol based tinctures may not be suitable for some patients because of the inherent concerns about alcohol consumption by patients. Further, tinctures are bulky and difficult to store.

It is desirable to develop a rapid and scalable process to produce a water-soluble powder that can be made using any cannabis extract. It is also desirable to develop a water-soluble powder comprising cannabis extract in order to precisely control dosage while administering cannabis extract to humans. Further, water-soluble powder is easier to store and carry.

The present invention describes a novel water-soluble powder composition comprising cannabis extract that produces a clear solution when mixed in water at various temperatures. Once solubilized in water, the cannabis extract does not separate from water even when the solution is frozen or thawed.

In one aspect, the invention describes a novel water-soluble powder composition comprising cannabis extract, ethanol, and isomalt. The ethanol is evaporated in the process of making the water-soluble powder. The water-soluble powder described in the invention produces a clear, tasteless solution when mixed with water and does not need a stabilizer such as citric acid. Once the water-soluble powder composition is dissolved in water, the cannabis extract does not separate from water when the solution is frozen and then thawed.

Determining a reliable and scalable method to produce water-soluble powder comprising cannabis extract has been difficult. The powder has to have the right texture. For example, if the powder comprises particles that are too fine, it may be difficult to pack. If the powder comprises particles that are too large, it may not dissolve readily. If the cannabis extract and polysaccharide powder are not properly mixed, then the powder composition upon mixing with water may result in cannabis extract separating from the polysaccharide powder. In earlier experimental processing methods, clumps would form when oil, isomalt, and alcohol were mixed but not sufficiently integrated. The clumps could be broken down by grinding to powder, but the resulting powder would not dissolve readily and floated in the water, often with oil droplets forming which then stuck to the walls of the vessel. This prevented it from forming a homogenous solution. The invention describes scalable methods to produce water-soluble powder composition comprising cannabis extract.

Further objectives and advantages, as well as the structure and function of preferred embodiments will become apparent from a consideration of the description and examples.

BRIEF DESCRIPTION OF THE DRAWINGS

FIG. 1 shows a method of preparing a water-soluble Cannabis powder composition.

SUMMARY OF THE INVENTION

In accordance with the invention, provided is a composition comprising a cannabis extract wherein the extract further comprises a polysaccharide and wherein the composition is water-soluble.

In one embodiment, the polysaccharide is selected from corn starch, coconut flour, potato starch, potato flour, arrowroot starch, Maltrin T-400, Microcrystalline Cellulose, Maltrin T-250, Uni-Pure WG220, Beta-Cyclodextrin, Isomalt 801, Isomalt 721, or a mixture thereof.

In one embodiment, the cannabis extract comprises cannabis oil or cannabis tincture. In another embodiment, the cannabis extract comprises a mixture of cannabinoids. In still another embodiment, the mixture of cannabinoids comprises tetrahydrocannabinol, tetrahydrocannabinolic acid, cannabidiol, cannabidiolic acid, cannabinol, cannabigerol, cannabichromene, cannabicyclol, cannabivarin, tetrahydrocannabivarin, cannabidivarin, cannabichromevarin, cannabigerovarin, cannabigerol monomethyl ether, cannabielsoin, or cannabicitran.

In one aspect, the mixture of cannabinoids comprises any two components selected from tetrahydrocannabinol, tetrahydrocannabinolic acid, cannabidiol, cannabidiolic acid, cannabinol, cannabigerol, cannabichromene, cannabicyclol, cannabivarin, tetrahydrocannabivarin, cannabidivarin, cannabichromevarin, cannabigerovarin, cannabigerol monomethyl ether, cannabielsoin, or cannabicitran. In another aspect, the mixture of cannabinoids comprises any two components selected from tetrahydrocannabinol, tetrahydrocannabinolic acid, cannabidiol, cannabidiolic acid, cannabinol, cannabigerol, cannabichromene, cannabicyclol, cannabivarin, tetrahydrocannabivarin, cannabidivarin, cannabichromevarin, cannabigerovarin, cannabigerol monomethyl ether, cannabielsoin, or cannabicitran, wherein the two components are in a ratio of about 1:20, about 1:10, or about 1:1.

In one embodiment, the cannabis extract comprises a terpenoid. In another embodiment, the cannabis extract comprises a mixture of terpenoids. In still another embodiment, the terpenoid is selected from alpha-bisabolol, borneol, alpha-caryophyllene, beta-caryophyllene, alpha elemene, beta elemene, gamma elemene, delta elemene, limonene, camphene, camphor, delta-3-carene, caryophyllene oxide, alpha-cedreen, citral, eucalyptol, beta-eudesmol, eudesm-7(11)-en-4-ol, farnesene, fenchol, alpha-guaiene, geraniol, guaiol, germacrene B, guaia-1(10)-11-diene, humulene, alpha-humulene, isobomeol, linalool, menthol, myrcene, alpha-myrcene, beta-myrcene, nerol, cis-ocimene, trans-ocimene, alpha-phellandrene, alpha-pinene, beta-pinene, pulegone, sabinene, alpha-terpinene, alpha-terpineol, terpinolene, terpineol, thymol, trans-2-pinanol, selina-3,7(1)-diene, or valencene. In still another embodiment, the terpenoid comprises terpenoid oil or terpenoid tincture. In yet another embodiment, the cannabis extract comprises a mixture of terpenoids and cannabinoids.

In one embodiment, the polysaccharide is a powder. In one aspect, the cannabis powder has a particle size of between about 200 to about 10 micrometer. In another embodiment, the cannabis powder has a particle size of about 180 to about 20 micrometers.

In accordance with the invention, further provided are methods of producing a water-soluble composition, wherein the water-soluble composition comprises a cannabis extract and wherein the extract further comprises a polysaccharide. In one embodiment, a method may comprise the steps of: mixing a cannabis extract with a solvent to make a first mixture; combining the first mixture with a polysaccharide to make a second mixture; drying the second mixture; and sifting the dried second mixture through a mesh; thereby producing a water-soluble composition. In another embodiment, the cannabis extract comprises cannabis oil or cannabis tincture. In still other embodiments, the cannabis extract comprises a mixture of cannabinoids. In yet other embodiments, the cannabinoids are selected from tetrahydrocannabinol, tetrahydrocannabinolic acid, cannabidiol, cannabidiolic acid, cannabinol, cannabigerol, cannabichromene, cannabicyclol, cannabivarin, tetrahydrocannabivarin, cannabidivarin, cannabichromevarin, cannabigerovarin, cannabigerol monomethyl ether, cannabielsoin, or cannabicitran. In one embodiment, the mixture of cannabinoids comprises any two components selected from tetrahydrocannabinol, tetrahydrocannabinolic acid, cannabidiol, cannabidiolic acid, cannabinol, cannabigerol, cannabichromene, cannabicyclol, cannabivarin, tetrahydrocannabivarin, cannabidivarin, cannabichromevarin, cannabigerovarin, cannabigerol monomethyl ether, cannabielsoin, or cannabicitran. In another embodiment, the mixture of cannabinoids comprises any two components in a ratio of about 1:20, about 1:10, or about 1:1.

In accordance with the invention, further provided are methods of producing a water-soluble composition comprising cannabis extract, wherein the cannabis extract comprises a terpenoid. In one embodiment, the cannabis extract comprises a mixture of terpenoids. In another embodiment, the terpenoid is selected from alpha-bisabolol, borneol, alpha-caryophyllene, beta-caryophyllene, alpha elemene, beta elemene, gamma elemene, delta elemene, limonene, camphene, camphor, delta-3-carene, caryophyllene oxide, alpha-cedreen, citral, eucalyptol, beta-eudesmol, eudesm-7(11)-en-4-ol, farnesene, fenchol, alpha-guaiene, geraniol, guaiol, germacrene B, guaia-1(10)-11-diene, humulene, alpha-humulene, isobomeol, linalool, menthol, myrcene, alpha-myrcene, beta-myrcene, nerol, cis-ocimene, trans-ocimene, alpha-phellandrene, alpha-pinene, beta-pinene, pulegone, sabinene, alpha-terpinene, alpha-terpineol, terpinolene, terpineol, thymol, trans-2-pinanol, selina-3,7(1)-diene, or valencene. In still another embodiment, the terpenoid comprises terpenoid oil or terpenoid tincture. In yet another embodiment, the cannabis extract comprises a mixture of terpenoids and cannabinoids.

In accordance with the invention, further provided are methods of producing a water-soluble composition wherein the solvent is selected from methanol, ethanol, propanol, butanol, or other alcohols, or a mixture thereof. In one embodiment, the solvent is ethanol.

In certain embodiments, the polysaccharide is a plant-based sugar. In other embodiments, the polysaccharide is a powder. In one embodiment, the powder has a particle size of between about 450 to about 1 micrometer, or between about 180 to about 10 micrometers. In other embodiments, the polysaccharide is selected from corn starch, coconut flour, potato starch, potato flour, arrowroot starch, Maltrin T-400, Microcrystalline Cellulose, Maltrin T-250, Uni-Pure WG220, Beta-Cyclodextrin, Isomalt 801, Isomalt 721, or a mixture thereof.

In accordance with the invention, further provided is a solution comprising water-soluble cannabis extract. Additionally, further provided is a frozen composition comprising water-soluble cannabis extract.

In accordance with the invention, further provided is a medication or a pharmaceutical composition or a kit comprising water-soluble cannabis extract. In other embodiments, further provided is a kit comprising a solution comprising water-soluble cannabis extract, or a frozen solution comprising water-soluble cannabis extract.

DETAILED DESCRIPTION OF THE INVENTION

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide a water-soluble powder composition comprising full-spectrum cannabis extract, or an oil comprising primarily an individual cannabinoid, or an oil comprising specific ratios of different cannabinoids, or an oil comprising on more cannabinoids and terpenoids, and methods to produce the water-soluble powder composition.

Embodiments of the invention are discussed in detail below. In describing embodiments of the invention, specific terminology is employed for the sake of clarity. However, the invention is not intended to be limited to the specific terminology so selected. While specific exemplary embodiments are discussed, it should be understood that this is done for illustration purposes only. A person skilled in the relevant art will recognize that other components and configurations can be used without parting from the spirit and scope of the invention. All references cited herein are incorporated by reference as if each had been individually incorporated.

In one aspect, the invention further describes a novel method of producing a water-soluble powder composition comprising cannabis extract, ethanol, and isomalt, that is rapid and scalable. For example, the invention describes a method for producing the water-soluble powder where the preparation time was reduced from seven days to as little as 20 minutes.

The term "cannabis extract" is used to refer to cannabis extracts that may contain cannabinoids and other beneficial components, such as terpenoids, or their synthetic derivatives or functional equivalents. Cannabis extract may be obtained through extraction processes utilizing carbon dioxide, butane, or ethanol, for example. In some embodiments, the cannabis extract comprises natural, neutral, or acidic forms of the cannabinoids, or semi-synthetic and synthetic derivatives thereof. In some embodiments, the cannabis extract comprises terpenoids and/or flavonoids. There are at least 144 cannabinoids that have been identified.

In one embodiment, cannabinoids may comprise any of THC (tetrahydrocannabinol), THCA (tetrahydrocannabinolic acid), CBD (cannabidiol), CBDA (cannabidiolic acid), CBN (cannabinol), CBG (cannabigerol), CBC (cannabichromene), CBL (cannabicyclol), CBV (cannabivarin), THCV (tetrahydrocannabivarin), CBDV (cannabidivarin), CBCV (cannabichromevarin), CBGV (cannabigerovarin), CBGM (cannabigerol monomethyl ether), CBE (cannabielsoin), or CBT (cannabicitran), for example. In another embodiment, cannabinoids may comprise a mixture of two or more of THC (tetrahydrocannabinol), THCA (tetrahydrocannabinolic acid), CBD (cannabidiol), CBDA (cannabidiolic acid), CBN (cannabinol), CBG (cannabigerol), CBC (cannabichromene), CBL (cannabicyclol), CBV (cannabivarin), THCV (tetrahydrocannabivarin), CBDV (cannabidivarin), CBCV (cannabichromevarin), CBGV (cannabigerovarin), CBGM (cannabigerol monomethyl ether), CBE (cannabielsoin), CBT (cannabicitran), among other compounds. In still another embodiment, cannabinoids may comprise a mixture of any two of THC (tetrahydrocannabinol), THCA (tetrahydrocannabinolic acid), CBD (cannabidiol), CBDA (cannabidiolic acid), CBN (cannabinol), CBG (cannabigerol), CBC (cannabichromene), CBL (cannabicyclol), CBV (cannabivarin), THCV (tetrahydrocannabivarin), CBDV (cannabidivarin), CBCV (cannabichromevarin), CBGV (cannabigerovarin), CBGM (cannabigerol monomethyl ether), CBE (cannabielsoin), CBT (cannabicitran), at a ratio of 1:40, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, or any ratio in between.

Terpenoids encompass a broad group of organic compounds that include terpenes, diterpenes, and sesquiterpenes. More than 100 different terpenoids have been detected in cannabis. In one embodiment, cannabis extract may comprise terpenoids. In another embodiment, terpenoids may comprise alpha-bisabolol, borneol, alpha-caryophyllene, beta-caryophyllene, elemene (alpha, beta, gamma, or delta), limonene, camphene, camphor, delta-3-carene, caryophyllene oxide, alpha-cedreen, citral, eucalyptol, beta-eudesmol, eudesm-7(11)-en-4-ol, farnesene, fenchol, alpha-guaiene, geraniol, guaiol, germacrene B, guaia-1(10)-11-diene, humulene, alpha-humulene, isobomeol, linalool, menthol, myrcene, alpha-myrcene, beta-myrcene, nerol, cis-ocimene, trans-ocimene, alpha-phellandrene, alpha-pinene, beta-pinene, pulegone, sabinene, alpha-terpinene, alpha-terpineol, terpinolene, terpineol, thymol, trans-2-pinanol, selina-3,7(1)-diene, or valencene.

In one exemplary embodiment, cannabis extract is added to the polysaccharide in order to achieve a final concentration of 9 mg THC per 500 mg of polysaccharide. In another embodiment, cannabis extract is added to the polysaccharide in order to achieve a final concentration of about 100, 90, 80, 70, 60, 50, 40, 30, 20, 19, 18, 17, 16, 15, 14, 13, 12, 11, 10, 9, 8, 7, 6, 5, 4, 3, 2, or 1 mg THC per 500 mg of polysaccharide, or any concentration in between.

FIG. 1 is a flow chart showing the method steps. The first step 10 is a measuring step and consists of a number of substeps in which the components are measured. In the first substep 12, the polysaccharide is measured. In the second substep 14, ethanol is measured, and in the third substep 16 the cannabis extract ("oil") is measured. The second main step 18 is a mixing step. In the first substep 20, the cannabis extract is mixed (dissolved into) the ethanol. In the second substep 22, the measured polysaccharide is placed into a mixing apparatus. In the third substep 24, the ethanolic cannabis solution is added to the polysaccharide. In the third substep 26, the fourth substep 28 and the fifth substep 30 details of the mixing regime are provided. The third main step 32 is a sifting and drying step. In the first substep 34, the mixture from substep 30 is sifted through a mesh onto a drying tray. In the second substep 36, the mixture on the tray is allowed to dry. In the third substep 38, the dried mixture is sifted to break up any clumps, and in the fourth substep 40, the sifted product is ready to be packaged.

In the process, the Cannabis extract is first dissolved in ethanol. The ethanol/cannabis extract mixture is then mixed with polysaccharide. In one embodiment, the amount of ethanol added is 10-50% of polysaccharide by weight. In another embodiment, the amount of ethanol added is 50-60% of polysaccharide by weight. In still another embodiment, the amount of ethanol added is 250-300% of polysaccharide by weight. In other embodiments, the amount of ethanol added is 1-10%, 60-250%, or 250-1000% of polysaccharide by weight, or any range in between. In yet other embodiments, cannabis extract may be dissolved into solvents such as methanol, ethanol, propanol, butanol, or other alcohols, or a mixture thereof.

In one embodiment, the polysaccharide is selected from any one of corn starch, coconut flour, potato starch, potato flour, or arrowroot starch. In another embodiment, the polysaccharide is selected from Maltrin T-400, Microcrystilline Cellulose, Maltrin T-250, Uni-Pure WG220 (Pregelatinized Corn Starch), Beta-Cyclodextrin, Milk powder, Isomalt 801, or Isomalt 721, or any combination thereof.

Isomalt 721 and Isomalt 801 have different solubility and different particle size for distribution in wet granulation, compaction and other agglomerations. Based on these differences between Isomalt 721 and Isomalt 801, different amounts of active ingredient can be incorporated into the mixture.

In one embodiment, the polysaccharide particle is 90 micrometers in size. In another embodiment, the polysaccharide particle is 180 micrometers in size. In yet another embodiment, the polysaccharide particle is about 450, 400, 350, 300, 250, 200, 150, 100, 50, or 1 micrometer in size. In still another embodiment, the polysaccharide particle is any size between about 450 and 1 micrometer.

The mixture comprising cannabis extract, polysaccharide, and ethanol is sifted through a mesh screen onto a tray.

Sifting is a process of putting a fine, loose, or powdery substance through a sieve so as to remove lumps or large particles. In one embodiment, the mesh screen is a 100-mesh screen. In another embodiment, the mesh screen is a 40-mesh screen. In still another embodiment, the mesh screen is a 50, 60, 70, 80, 100, 120, 140, 170, 200, 230, 270, 325, 400, 450, 500, 635, 1200, 1250, 2500-mesh screen, or any number in between.

In one embodiment, the mesh screen pores are 250 micrometers in size. In still another embodiment, the mesh screen pores are about 5, 7, 10, 12, 20, 25, 32, 37, 44, 53, 63, 74, 88, 105, 125, 149, 177, 210, 250, or 297 micrometers in size, or any size in between.

In one exemplary embodiment, the sifted powder may have a size of 149 micrometers. In another embodiment, the sifted powder may have a size of 200, 190, 180, 170, 160, 150, 140, 130, 120, 110, 100, 90, 80, 70, 60, 50, 40, 30, 20, 10, 9, 8, 7, 6, or 5 micrometer, or any size in between.

Any alterations and further modifications of the compositions and/or formulations described herein, which would normally occur to one skilled in the relevant art and having possession of this disclosure, are to be considered within the scope of the instant claims.

EXAMPLES

Example 1

Powder Experiments with Corn Starch, Coconut Flour, Potato Starch, and Potato Flour Various polysaccharides were tested as the base for a powdered cannabis product. The different polysaccharides were tested for ease of mixing, homogeneity, particle size once mixed (clumping), solubility in room temperature water, hot water and cold water.

WB Refined oil (cannabis oil) was obtained by carbon dioxide extraction. In addition to carbon dioxide extraction, cannabis oil can be extracted using water extraction, ethanol extraction and extraction methods that leave no residual solvents. After cannabis oil is extracted, an additional step called de-waxing (AKA "winterizing") was carried out. De-waxing is a post-processing technique used for extracted cannabis oils. De-waxing further removes plant waxes, fats, and lipids from the carbon dioxide extracted oil, leaving a thinner, less viscous, and slightly more concentrated product. Ethanol and below-freezing temperatures were used to separate and remove all remaining waxy materials. The ethanol was then distilled off using a rotary evaporator or other distillation technique. All of the aforementioned methodologies create a cannabis oil product that lends itself to powderization through the addition of a polysaccharide.

WB Refine oil has 80.83% THC. Therefore, 11.13 mg of WB Refine oil was added to 488.87 g of powder to achieve a final concentration of 9 mg THC per 500 mg of powder.

| | | | |
|---|---|---|---|
| Cannabis Oil (WB Refine oil): | 11.13 mg | ×10 | 111.3 mg |
| Polysaccharide: | 488.87 mg | ×10 | 4888.7 mg |

The following protocol for mixing was used:
1. Weigh 111.3 mg WB Refine oil (cannabis oil) into a clean tared 20 mL glass beaker
2. Dissolve cannabis oil into 5 g of 100% ethanol, low heat can be applied to increase the speed of dissolution.
3. Weigh out 4888.7 mg of the polysaccharide
4. Slowly add the weighed powder to the ethanol/cannabis oil mixture
5. Heat the mixture at 100° C.
6. Continually mix until the ethanol has completely evaporated
7. Once dry break up the mixture into a fine powder
8. Repeat for all polysaccharides
9. Record observations for each polysaccharide.

Powder Experiment with Arrowroot Starch

Powdered arrowroot starch was used as the base for a powdered cannabis product. Arrowroot starch was tested for the ease of mixing, homogeneity, particle size once mixed (clumping), solubility in room temperature water, solubility in hot water, and solubility in cold water. The same formula and mixing protocol was used. Cold-water solubility and mix solubility tests were also conducted.

Cold Water Solubility Tests

Cold water solubility tests on corn starch, coconut flour, potato starch, and potato flour mixtures were conducted.

TABLE 1

Powder properties and solubility tests

| Polysaccharide | Mixing ease | Visual | Flowability | Particle Size | Solubility (Room Temp) | Solubility (Hot) | Solubility (Cold) | Sediment |
|---|---|---|---|---|---|---|---|---|
| Corn Starch | Moderate | Even color | Medium | Non-uniform | YES | YES | YES | YES |
| Coconut Flour | Moderate | Even color | Medium | Non-uniform | YES | YES | YES | YES |
| Potato Starch | Moderate | Even color | Low | Segregation | YES | NO | NO | YES |
| Potato Flour | Moderate | Even color | Low | Segregation | YES | YES | YES | YES |
| Arrowroot | Easy | Even color | Medium | Non-uniform | YES | NO | YES | YES |
| Isomalt | Very Nice | Even Color | High | Uniform | YES | YES | YES | NO |

TABLE 2

Powder properties and solubility tests:

| Polysaccharide | Mixing ease | Visual | Flowability | Particle Size | Solubility (Room Temp) | Solubility (Hot) | Solubility (Cold) | Sediment |
|---|---|---|---|---|---|---|---|---|
| Maltrin T-400 Microcrystilline Cellulose Etain - Forte Cannabis Oil | Moderate | Even color | Medium | Non-uniform | YES | YES | YES | YES |
| Maltrin T-400 Etain - Forte Cannabis Oil | Moderate | Even color | Medium | Non-uniform | YES | YES | YES | YES |
| Maltrin T-250 Etain - Forte Cannabis Oil | Moderate | Even color | Medium | Non-uniform | YES | YES | NO | YES |
| Uni-Pure WG220 (Pregelatinized Corn Starch) Microcrystalline cellulose Etain - Forte Cannabis Oil | Difficult | Even Color | Low | Non-uniform | YES | YES | NO | YES |
| Beta-Cyclodextrin Etain - Forte Cannabis Oil | Moderate | Even Color | Medium | Non-uniform | YES | YES | YES | YES |
| 50/50 dry component mix Milk powder Maltrin T-400 Etain - Forte Cannabis oil | Difficult | Uneven color | Medium | Non-uniform | NO | YES | NO | YES |
| 75/25 dry component mix Milk powder Maltrin T-400 Etain - Forte Cannabis oil | Difficult | Uneven Color | Medium | Non-uniform | NO | YES | NO | YES |
| Isomalt 801 Etain - Forte Cannabis Oil | Easy | Even color | High | Uniform | YES | YES | YES | NO |
| Isomalt 721 Etain - Forte Cannabis Oil | Easy | Even color | High | Uniform | YES | YES | YES | YES |

Example 2

Methods of Preparing Powder Composition
Method: 1
1. Measuring (10):
   a. Measure the amount of polysaccharide (12) that is chosen for the process based upon the volume and quantity the vessel can hold (5 kg). The polysaccharide particle size was 90 micrometers.
   b. Measure the ethanol (14) needed for the required batch (10%-50% to polysaccharide weight).
   c. Measure the amount of cannabis (16) oil needed per batch based upon dose. The Cannabis oil may be obtained through carbon dioxide, butane, or ethanol extraction.
2. Mixing (18):
   a. Mix cannabis oil with ethanol into one homogeneous solution (20). Cannabis oil is soluble in ethanol.
   b. Place polysaccharide in a mixing bowl and form a deep well (22).
   c. Pour the ethanol/cannabis oil solution into the deep well (24).
   d. Whisk to mix solution at 84 RPM in a Plantar Mixer Model ADCRPM-30 for up to 5 minutes (26). Scrape sides and bottom of mixture to ensure all ingredients are fully mixed.
   e. Continue mixing again at 151 RPM a Plantar Mixer Model ADCRPM-30 for up to 5 minutes (28). Scrape sides and bottom of mixture to insure all ingredients are fully mixed.
   f. Repeat this process again at 270 RPM a Plantar Mixer Model ADCRPM-30 for between 1 to 5 additional minutes until homogenous (30).
3. Sifting & Drying (32):
   a. Sift the mixture through a 100-mesh screen onto a tray (34). Sift no more than 1 kilogram of the mixture per tray. Spread the mixture on a the tray. Avoid compressing when spreading the mixture. The drying tray size is 18"×26"×1" but can vary depending on the amount of powder being processed.
   b. Let it dry between 20 minutes to 48 hours (36). A Powder Flow Dryer, or a Fluid Bed Dryer, or a Rotary Dryer or other similar drying systems may be used to decrease drying time.
   c. Finally, sift again through a 120-mesh (38). A vibrating sieve or cone mill sieve sifter is used to sift the final material.
   d. Powder is ready to be packaged (40).

Method: 2

Measuring:
a. Measure the amount of polysaccharide that is chosen for the process based upon the volume and quantity the vessel can hold (5 kg). The polysaccharide particle size was 180 micrometers.
b. Measure the ethanol needed for the required batch (50%-60% to polysaccharide weight).
c. Measure the amount of cannabis oil needed per batch based upon dose.

Mixing:
a. Mix cannabis oil with ethanol into one homogenized solution.
b. Place polysaccharide in a mixing bowl and form a deep well.
c. Pour the ethanol/cannabis oil solution into the deep well.
d. Use a whisk to mix solution at the lowest speed for up to 5 minutes. Scrape sides and bottom of mixture to insure all ingredients are fully mixed.
e. Continue mixing again at medium speed for up to 5 minutes. Scrape sides and bottom of mixing bowl to ensure all ingredients are fully mixed
f. Repeat this process again at medium speed for up to 5 additional minutes.

Drying:
a. Place powder on drying trays or baking sheets. Use no more than 1 kilogram per tray. Preferably, the powder is poured onto drying trays and a spatula is used to spread the powder evenly across the surface of the drying tray. The spatula is held at a 90-degree angle from the drying tray so as not to compact or compress the powder.
b. Let it dry for up to 48 hours.

Grinding and Sifting:
a. Grind dried powder through sugar grinder to a consistency of confection powder.
b. Sift through a 40-mesh screen.
c. Powder is ready to be packaged.

Method 1 is preferred to Method 2 because Method 2 requires grinding, which also makes packaging and handling of final powder more difficult due to lower flowability of the final product. Additionally, Method 1 is preferred to Method 2 because Method 2 requires the use of a higher concentration of ethanol which leads to longer drying times.

Method: 3

Measuring:
a. Measure the amount of polysaccharide that is chosen for the process based upon the volume and quantity the vessel can hold (5 kg). The polysaccharide particle size was 180 micrometers.
b. Then measure the ethanol needed for the required batch (250%-300% to polysaccharide weight).
c. Measure the amount of cannabis oil needed per batch based upon dose.

Mixing:
a. Mix cannabis oil with ethanol into one homogenized solution.
b. Pour the ethanol/cannabis oil solution into the mixing vessel.
c. Add polysaccharide to the mixing vessel and mix well.
d. Use a spatula to mix the solution.
e. Continue mixing again on medium speed for up to 5 minutes. Scrape sides and bottom of mixing bowl to insure all ingredients are fully mixed.
f. Repeat this process again on medium speed for up to 5 additional minutes.

Drying:
a. Place powder on drying trays or baking sheets. Use no more than 1 kilogram per tray. Spread the mixture on the drying tray or baking sheet. Avoid compressing when spreading the mixture. Spatula needs to be 90 degrees or less to the drying tray.
b. Let it dry from 72 to 168 hours.

Grinding and Sifting:
a. Grind dried powder through sugar grinder to a consistency of confection powder.
b. Sift through a 40-mesh screen (250-micrometer mesh).
c. The powder is ready to be packaged.

Method 1 is preferred to Method 3 because Method 3 requires a longer drying time and it requires the use of a higher concentration of ethanol.

Example 3

Powder Solubility Test

Solubility of each powder was observed at multiple temperature ranging from 0° C. to 100° C. For each experiment, ⅛ teaspoon of the powder was placed into 250 mL of water at a specific temperature, observed for a few seconds, and then stirred.

At 0° C. the powder initially sat on top of the water then began to slowly fall after a few seconds. The powder then clumped at the bottom. After stirring was initiated, the mixture had floaters and sinkers. After 2 minutes of stirring the powder was mostly in solution with some floaters on top but the clumps were gone. There was some residue on the glass container surface and on the stirring rod. After stirring for an hour the powder dissolved completely and the solution temperature had risen to 12° C., with no remaining residue. The solution was slightly cloudy.

At 10° C. the powder initially sat on top of the water for a few seconds and then slowly fell to the bottom. There were some clumps at the bottom. The powder dissolved after 45 seconds of stirring and the clumps at the bottom disappeared. There was a slight residue on the glass container surface and on the stirring rod. After stirring for an hour the powder dissolved completely and the solution temperature had risen to 17° C., with no remaining residue. The solution was slightly cloudy.

At 21° C. (room temperature) the powder sat on top momentarily and then fell into the mixture steadily. There were a few clumps at the bottom. The powder dissolved completely after 20 seconds of stirring, with no visible clumps or residue on the glass container surface or on the stirring rod. The solution was slightly cloudy.

At 60° C. the powder fell into the mixture immediately and a very small amount settled onto the bottom. The clumps at the bottom were very small and went into solution immediately upon stirring, with no visible clumps or residues on the glass container surface or on the stirring rod. The solution was slightly cloudy.

At 100° C. the powder dissolved immediately without any stirring. There were no visible clumps or residues on the glass container surface or on the stirring rod. The solution was slightly cloudy.

Freezing

A solution heated at 100° C. was cooled and then frozen. Once completely frozen the solution was removed from the freezer and then allowed to melt at room temperature overnight. When the solution was observed the next morning, the powder had remained in solution and the solution was still slightly cloudy, with a slight sheen on top of the solution.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

What is claimed is:

1. A synthetic cannabis formulation consisting essentially of synthetic cannabis, coconut flour, isomalt, a starch selected from the group consisting of corn starch, potato starch, arrowroot starch and mixtures thereof.

2. The composition of claim 1, wherein the isomalt is isomalt 721, isomalt 801 or a mixture thereof.

3. The composition of claim 1, wherein the synthetic cannabis consists essentially of a mixture of synthetic cannabinoids.

4. The composition of claim 3, wherein the mixture of synthetic cannabinoids are selected from the group consisting of tetrahydrocannabinol, tetrahydrocannabinolic acid, cannabidiol, cannabidiolic acid, cannabinol, cannabigerol, cannabichromene, cannabicyclol, cannabivarin, tetrahydrocannabivarin, cannabidivarin, cannabichromevarin, cannabigerovarin, cannabigerol monomethyl ether, cannabielsoin, and cannabicitran.

5. The composition of claim 4, wherein the mixture of synthetic cannabinoids are two selected from the group consisting of selected from tetrahydrocannabinol, tetrahydrocannabinolic acid, cannabidiol, cannabidiolic acid, cannabinol, cannabigerol, cannabichromene, cannabicyclol, cannabivarin, tetrahydrocannabivarin, cannabidivarin, cannabichromevarin, cannabigerovarin, cannabigerol monomethyl ether, cannabielsoin, and cannabicitran.

6. The composition of claim 5, wherein the two components are selected from the group consisting of tetrahydrocannabinol, tetrahydrocannabinolic acid, cannabidiol, cannabidiolic acid, cannabinol, cannabigerol, cannabichromene, cannabicyclol, cannabivarin, tetrahydrocannabivarin, cannabidivarin, cannabichromevarin, cannabigerovarin, cannabigerol monomethyl ether, cannabielsoin, and cannabicitran, are in a ratio of about 1:20.

7. The composition of claim 5, wherein the two components are selected from the group consisting of tetrahydrocannabinol, tetrahydrocannabinolic acid, cannabidiol, cannabidiolic acid, cannabinol, cannabigerol, cannabichromene, cannabicyclol, cannabivarin, tetrahydrocannabivarin, cannabidivarin, cannabichromevarin, cannabigerovarin, cannabigerol monomethyl ether, cannabielsoin, and cannabicitran, are in a ratio of about 1:10.

8. The composition of claim 5, wherein the two components are selected from the group consisting of tetrahydrocannabinol, tetrahydrocannabinolic acid, cannabidiol, cannabidiolic acid, cannabinol, cannabigerol, cannabichromene, cannabicyclol, cannabivarin, tetrahydrocannabivarin, cannabidivarin, cannabichromevarin, cannabigerovarin, cannabigerol monomethyl ether, cannabielsoin, and cannabicitran, are in a ratio of about 1:1.

9. The composition of claim 1, further consisting essentially of a terpenoid or a mixture of terpenoids.

10. The composition of claim 9, wherein the terpenoid is selected from the group consisting of alpha-bisabolol, borneol, alpha-caryophyllene, beta-caryophyllene, alpha elemene, beta elemene, gamma elemene, delta elemene, limonene, camphene, camphor, delta-3-carene, caryophyllene oxide, alpha-cedreen, citral, eucalyptol, beta-eudesmol, eudesm-7(11)-en-4-ol, farnesene, fenchol, alpha-guaiene, geraniol, guaiol, germacrene B, guaia-1(10)-11-diene, humulene, alpha-humulene, isobomeol, linalool, menthol, myrcene, alpha-myrcene, beta-myrcene, nerol, cis-ocimene, trans-ocimene, alpha-phellandrene, alpha-pinene, beta-pinene, pulegone, sabinene, alpha-terpinene, alpha-terpineol, terpinolene, terpineol, thymol, trans-2-pinanol, selina-3,7(1)-diene, valencene and mixtures thereof.

11. The composition of claim 1, wherein the formulation is water soluble.

12. A solution consisting essentially of the formulation of claim 1.

13. A frozen composition consisting essentially of the formulation of claim 1.

14. A medicament consisting essentially of the formulation of claim 1.

15. A pharmaceutical composition consisting essentially of the formulation of claim 1.

16. A kit consisting essentially of the formulation of claim 1.

17. A method of producing the formulation of claim 1, consisting essentially of:
mixing synthetic cannabis with isomalt to make a first mixture;
combining the first mixture with coconut flour to make a second mixture;
mixing the second mixture with starch to make a third mixture;
drying the third mixture; and
sifting the dried third mixture through a mesh, thereby producing the formulation of claim 1.

18. The method of claim 17, wherein the synthetic cannabis consists essentially of a mixture of cannabinoids.

19. The method of claim 18, wherein the cannabinoids are selected from the group consisting of tetrahydrocannabinol, tetrahydrocannabinolic acid, cannabidiol, cannabidiolic acid, cannabinol, cannabigerol, cannabichromene, cannabicyclol, cannabivarin, tetrahydrocannabivarin, cannabidivarin, cannabichromevarin, cannabigerovarin, cannabigerol monomethyl ether, cannabielsoin, and cannabicitran.

20. The method of claim 19, wherein the components are two selected from the group consisting of tetrahydrocannabinol, tetrahydrocannabinolic acid, cannabidiol, cannabidiolic acid, cannabinol, cannabigerol, cannabichromene, cannabicyclol, cannabivarin, tetrahydrocannabivarin, cannabidivarin, cannabichromevarin, cannabigerovarin, cannabigerol monomethyl ether, cannabielsoin, and cannabicitran.

21. The method of claim 19, wherein the components are two selected from the group consisting of tetrahydrocannabinol, tetrahydrocannabinolic acid, cannabidiol, cannabidiolic acid, cannabinol, cannabigerol, cannabichromene, cannabicyclol, cannabivarin, tetrahydrocannabivarin, cannabidivarin, cannabichromevarin, cannabigerovarin, cannabigerol monomethyl ether, cannabielsoin, and cannabicitran, in a ratio of about 1:20.

22. The method of claim 19, wherein the components are two selected from the group consisting of tetrahydrocannabinol, tetrahydrocannabinolic acid, cannabidiol, cannabidiolic acid, cannabinol, cannabigerol, cannabichromene, cannabicyclol, cannabivarin, tetrahydrocannabivarin, cannabidivarin, cannabichromevarin, cannabigerovarin, cannabigerol monomethyl ether, cannabielsoin, and cannabicitran, in a ratio of about 1:10.

23. The method of claim 19, wherein the components are two selected from the group consisting of tetrahydrocannabinol, tetrahydrocannabinolic acid, cannabidiol, cannabidiolic acid, cannabinol, cannabigerol, cannabichromene, cannabicyclol, cannabivarin, tetrahydrocannabivarin, cannabidivarin, cannabichromevarin, cannabigerovarin, cannabigerol monomethyl ether, cannabielsoin, and cannabicitran, in a ratio of about 1:1.

24. The method of claim 17, further consisting essentially of a terpenoid or a mixture of terpenoids.

25. The method of claim 24, wherein the terpenoid is selected from the group consisting of alpha-bisabolol, borneol, alpha-caryophyllene, beta-caryophyllene, alpha elemene, beta elemene, gamma elemene, delta elemene, limonene, camphene, camphor, delta-3-carene, caryophyllene oxide, alpha-cedreen, citral, eucalyptol, beta-eudesmol, eudesm-7(11)-en-4-ol, farnesene, fenchol, alpha-guaiene, geraniol, guaiol, germacrene B, guaia-1(10)-11-diene, humulene, alpha-humulene, isoborneol, linalool, menthol, myrcene, alpha-myrcene, beta-myrcene, nerol, cis-ocimene, trans-ocimene, alpha-phellandrene, alpha-pinene, beta-pinene, pulegone, sabinene, alpha-terpinene, alpha-terpineol, terpinolene, terpineol, thymol, trans-2-pinanol, selina-3,7(1)-diene, valencene and mixtures thereof.

26. The method of claim 17, wherein the coconut flour is a powder.

* * * * *